(12) United States Patent
Shimazu et al.

(10) Patent No.: US 11,554,089 B2
(45) Date of Patent: Jan. 17, 2023

(54) HAIR COSMETIC

(71) Applicant: KAO CORPORATION, Chuo-ku (JP)

(72) Inventors: Ayako Shimazu, Arakawa-ku (JP); Ayami Nagayama, Mizuho (JP)

(73) Assignee: KAO CORPORATION, Chuo-ku (JP)

(*) Notice: Subject to any disclaimer, the term of this patent is extended or adjusted under 35 U.S.C. 154(b) by 19 days.

(21) Appl. No.: 16/765,067

(22) PCT Filed: Nov. 19, 2018

(86) PCT No.: PCT/JP2018/042713
§ 371 (c)(1),
(2) Date: May 18, 2020

(87) PCT Pub. No.: WO2019/098375
PCT Pub. Date: May 23, 2019

(65) Prior Publication Data
US 2020/0360256 A1 Nov. 19, 2020

(30) Foreign Application Priority Data

Nov. 20, 2017 (JP) .............................. JP2017-223224
Apr. 13, 2018 (JP) .............................. JP2018-078016

(51) Int. Cl.
*A61K 8/49* (2006.01)
*A61K 8/41* (2006.01)
*A61K 8/86* (2006.01)
(Continued)

(52) U.S. Cl.
CPC .............. *A61K 8/492* (2013.01); *A61K 8/416* (2013.01); *A61K 8/86* (2013.01); *A61K 8/891* (2013.01);
(Continued)

(58) Field of Classification Search
CPC .................... A61K 8/891; A61K 8/898; A61K 2800/594; A61K 8/062; A61K 8/86; A61K 2800/412; A61K 2800/43; A61K 2800/59; A61K 8/416; A61K 8/492; A61K 2800/21; A61K 2800/5426; A61K 2800/63; A61K 2800/651; A61K 2800/88; A61K 8/0241; A61K 8/06; A61K 8/27; A61K 8/29; A61K 8/44; A61K 8/498; A61K 8/585; A61K 8/731; A61K 8/817; A61K 8/8182; A61K 8/894; A61K 8/0279; A61K 8/65; A61K 8/73; A61K 8/736; A61K 8/91; A61K 8/046; A61K 2800/596; A61K 2800/87; A61K 8/31; A61K 8/463; A61K 8/342; A61K 8/315; A61K 8/4926; A61K 8/4933; A61K 2800/5424; A61K 8/068; A61K 2800/413; A61K 8/345; A61K 8/442; A61K 8/892; A61K 8/895; A61K 31/4412; A61K 8/25; A61K 8/893; A61K 2800/80; A61K 8/69; A61K 8/92; A61K 2800/10; A61K 2800/58; A61K 31/60; A61K 8/365; A61K 8/37; A61K 8/737; A61K 2800/30; A61K 8/466; A61K 8/8152; A61K 8/89; A61K 8/19; A61K 2800/48; A61K 2800/544; A61K 31/4164; A61K 8/39;
(Continued)

(56) References Cited

U.S. PATENT DOCUMENTS 7,857,862 B2 12/2010 Koike et al.
2008/0050330 A1 2/2008 Ishino
(Continued)

FOREIGN PATENT DOCUMENTS

CN 102046145 5/2011
CN 102665670 9/2012
(Continued)

OTHER PUBLICATIONS

U.S. Appl. No. 16/765,061, filed May 18, 2020, Sakai, Yuta et al.
International Search Report dated Feb. 26, 2019 in PCT/JP2018/042713 filed Nov. 19, 2018, 2 pages.
Extended European Search Report dated Jul. 28, 2021 in European Patent Application No. 18878721.2, 5 pages.
Organosilicon Material, Jikai Zhang, 1999, p. 83 and 2 cover pages.
(Continued)

*Primary Examiner* — Audrea B Coniglio
(74) *Attorney, Agent, or Firm* — Oblon, McClelland, Maier & Neustadt, L.L.P.

(57) ABSTRACT

The present invention relates to a hair cosmetic containing the following components (A) to (C):
(A) a compound represented by the following general formula (1) or a salt thereof:

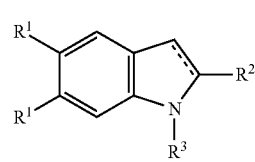

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;
(B) a dimethylsilicone; and
(C) an amino-modified silicone,
the hair cosmetic satisfying such conditions that a mass ratio of the component (C) to the component (B) [(C)/(B)] is 0.3 or more and 3.0 or less; and a mass ratio of the component (A) to the component (B) and component (C) {(A)/[(B)+(C)]} is 1.0 or less.

11 Claims, No Drawings

(51) Int. Cl.
*A61K 8/891* (2006.01)
*A61K 8/898* (2006.01)
*A61Q 5/06* (2006.01)

(52) U.S. Cl.
CPC .............. *A61K 8/898* (2013.01); *A61Q 5/065* (2013.01); *A61K 2800/43* (2013.01); *A61K 2800/59* (2013.01)

(58) Field of Classification Search
CPC ............ A61K 2800/22; A61K 2800/54; A61K 2800/592; A61K 2800/614; A61K 2800/884; A61K 33/38; A61K 36/185; A61K 8/0208; A61K 8/042; A61K 8/044; A61K 8/20; A61K 8/34; A61K 8/36; A61K 8/49; A61K 8/604; A61K 8/64; A61K 8/70; A61K 8/896; A61K 2300/00; A61K 2800/57; A61K 2800/612; A61K 2800/654; A61K 2800/81; A61K 2800/94; A61K 31/555; A61K 8/0254; A61K 8/26; A61K 8/28; A61K 8/35; A61K 8/362; A61K 8/368; A61K 8/41; A61K 8/42; A61K 8/4913; A61K 8/494; A61K 8/4946; A61K 8/58; A61K 8/602; A61K 8/8129; A61K 8/8176; A61K 9/0014; A61K 9/107; A61K 2800/262; A61K 2800/28; A61K 2800/4324; A61K 2800/49; A61K 2800/52; A61K 2800/524; A61K 2800/5428; A61K 2800/623; A61K 2800/624; A61K 2800/95; A61K 31/4174; A61K 47/34; A61K 47/44; A61K 47/62; A61K 47/6435; A61K 47/6843; A61K 8/0212; A61K 8/022; A61K 8/0245; A61K 8/0291; A61K 8/066; A61K 8/361; A61K 8/676; A61K 8/8147; A61K 8/899; A61K 9/06; A61K 9/14; A61Q 5/00; A61Q 5/10; A61Q 5/12; A61Q 15/00; A61Q 19/10; A61Q 5/02; A61Q 5/065; A61Q 17/04; A61Q 19/08; A61Q 1/02; A61Q 1/06; A61Q 5/06; A61Q 5/08; A61Q 7/00; A61Q 19/00; A61Q 5/006; A61Q 1/10; A61Q 1/12; A61Q 5/002; A61Q 1/04; A61Q 1/08; A61Q 19/002; A61Q 1/00; A61Q 1/14; A61Q 11/00; A61Q 13/00; A61Q 19/04; A61Q 5/04; A61Q 19/004; A61Q 19/007; A61Q 19/02; A61Q 3/00; A61Q 17/00; A61Q 19/001; A61Q 5/004; A45D 34/00; A45D 19/005; A45D 19/0066

See application file for complete search history.

(56) References Cited

U.S. PATENT DOCUMENTS

| | | |
|---|---|---|
| 2010/0037404 A1 | 2/2010 | Koike et al. |
| 2010/0154135 A1 | 6/2010 | Matsunaga et al. |
| 2010/0170048 A1 | 7/2010 | Koike et al. |

FOREIGN PATENT DOCUMENTS

| | | |
|---|---|---|
| EP | 1 894 556 A2 | 3/2008 |
| EP | 2 030 606 A1 | 3/2009 |
| JP | 2004-35493 A | 2/2004 |
| JP | 2007-326812 A | 12/2007 |
| JP | 5363703 B2 | 12/2013 |
| JP | 2014-114264 | 6/2014 |
| WO | WO 2008/149535 A1 | 12/2008 |

HAIR COSMETIC

FIELD OF THE INVENTION

The present invention relates to a hair cosmetic.

BACKGROUND OF THE INVENTION

Conventionally, as a hair dye for gray hair dyeing, an air-oxidative hair dye using 5,6-dihydroxyindole, 5,6-dihydroxyindoline, or a derivative thereof, each of which is a melanin precursor, is known. Such a melanin precursor does not use an oxidizing agent, and therefore, even in the case of being used for a hair dye, it is less in damage of the hair, and it is high in convenience as a dye for hair dye.

On the other hand, in hairs treated with a hair dye containing the aforementioned melanin precursor, peculiar squeaky feeling is generated, and hardness or stiff feeling is brought. Thus, it was hardly said that the foregoing hair dye is on a level sufficiently satisfactory from the standpoint of touch of hair after the treatment. Then, for example, PTL 1 proposes a hair dye composition which contains, in addition to the aforementioned melanin precursor, a silicone, such as an amino-modified silicone, and a polyhydric alcohol and is excellent in dyeing properties, touch, and usability.

CITATION LIST

Patent Literature

PTL 1: JP 2007-326812 A

SUMMARY OF THE INVENTION

The present invention relates to the following.
[1] A hair cosmetic containing the following components (A) to (C):

(A) a compound represented by the following general formula (1) or a salt thereof:

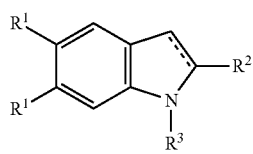

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a dimethylsilicone; and (C) an amino-modified silicone, the hair cosmetic satisfying such conditions that a mass ratio of the component (C) to the component (B) [(C)/(B)] is 0.3 or more and 3.0 or less; and a mass ratio of the component (A) to the component (B) and component (C) {(A)/[(B)+(C)]} is 1.0 or less.

DETAILED DESCRIPTION OF THE INVENTION

[Hair Cosmetic]

The hair cosmetic of the present invention is a hair cosmetic containing the following components (A) to (C):

(A) a compound represented by the following general formula (1) or a salt thereof:

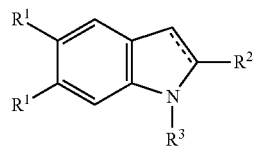

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a dimethylsilicone; and (C) an amino-modified silicone, the hair cosmetic satisfying such conditions that a mass ratio of the component (C) to the component (B) [(C)/(B)] is 0.3 or more and 3.0 or less; and a mass ratio of the component (A) to the component (B) and component (C) {(A)/[(B)+(C)]} is 1.0 or less.

In view of the fact that the hair cosmetic of the present invention has the aforementioned constitution, even when it contains the component (A), squeaky feeling during rinsing of hair after the treatment with the foregoing hair cosmetic and squeaky feeling of the hair resulting from, after the treatment, performing rinsing and drying, and then further shampooing can be improved. In addition, it is able to readily perform dyeing of gray hair and the like through a daily hair care behavior.

When a silicone is blended in a composition containing the component (A) that is a melanin precursor, the hardness or stiff feeling during drying of hair after the treatment with the foregoing composition is relaxed. But, it has been found that during rinsing of hair on washing away of the composition after the treatment, or during rinsing of hair resulted when, after the treatment, rinsing and drying are performed, and from the following day, shampooing is further performed to wash away the silicone, the peculiar squeaky feeling is generated on the aforementioned melanin precursor.

In a hair cosmetic containing a predetermined melanin precursor, a problem of the present invention is to improve squeaky feeling during rinsing of hair after the treatment as well as squeaky feeling during rinsing of hair resulted when after the treatment, rinsing and drying are performed, and shampooing is further performed.

The present inventors have found that the aforementioned problem can be solved by a hair cosmetic containing a predetermined melamine precursor and a dimethylsilicone and an amino-modified silicone in specified ratios.

In accordance with the hair cosmetic of the present invention, it is possible to improve the squeaky feeling during rinsing of hair after the treatment as well as the squeaky feeling during rinsing of hair resulted when after the treatment, rinsing and drying are performed, and shampooing is further performed and to improve the touch of hair after the treatment.

In the present invention, examples of the hair cosmetic include a hair cleansing agent, such as a shampoo, a hair rinse, a hair conditioning agent, a hair treatment agent, a hair styling agent, a hair dye, and a hair growth promoter. Of these, a hair cosmetic selected from the group consisting of a hair rinse, a hair conditioning agent, and a hair treatment agent is preferred.

The formulation of the hair cosmetic is not particularly limited, and it is possible to take an arbitrary formulation, for example, a liquid, a foam, a paste, a cream, a solid, and a powder. From the viewpoint of applicability on the hair, the formulation is preferably a liquid, a paste, or a cream.

<Component (A)>

The hair cosmetic of the present invention contains the component (A) that is a compound represented by the following general formula (1) or a salt thereof. The component (A) is a melanin precursor which is polymerized through air oxidation and converted to a melanin precursor and acts as a dyeing agent of hair.

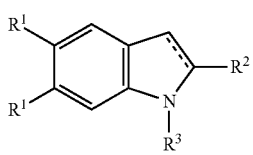

(1)

In the formula, a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group.

The melanin precursor of the component (A) is an indole derivative or an indoline derivative that is the compound represented by the general formula (1), or a salt thereof, and in the present invention, one or a combination of two or more thereof can be used. From the viewpoint of hair dyeing properties, the component (A) is more preferably an indole derivative (namely, a π bond exists in the broken line portion in the general formula (1)).

From the viewpoint of availability and hair dyeing properties of the component (A), in the general formula (1), $R^1$ is preferably a hydroxy group; $R^2$ is preferably a hydrogen atom or —COOR (R is a hydrogen atom, a methyl group, or an ethyl group), and more preferably a hydrogen atom or —COOH; and $R^3$ is preferably a hydrogen atom.

Examples of the compound represented by the general formula (1) include 5,6-dihydroxyindole, 5,6-dihydroxyindole-2-carboxylic acid, methyl 5,6-dihydroxyindole-2-carboxylate, ethyl 5,6-dihydroxyindole-2-carboxylate, N-methyl-5,6-dihydroxyindole, N-methyl-5,6-dihydroxyindole-2-carboxylic acid, N-ethyl-5,6-dihydroxyindole, N-ethyl-5,6-dihydroxyindole-2-carboxylic acid, N-acetyl-5,6-dihydroxyindole, N-acetyl-5,6-dihydroxyindole-2-carboxylic acid, 5-acetoxy-6-hydroxyindole, 5-acetoxy-6-hydroxyindole-2-carboxylic acid, 5,6-dihydroxyindoline, 5,6-dihydroxyindoline-2-carboxylic acid, methyl 5,6-dihydroxyindoline-2-carboxylate, ethyl 5,6-dihydroxyindoline-2-carboxylate, N-methyl-5,6-dihydroxyindoline, N-methyl-5,6-dihydroxyindoline-2-carboxylic acid, N-ethyl-5,6-dihydroxyindoline, N-ethyl-5,6-dihydroxyindoline-2-carboxylic acid, N-acetyl-5,6-dihydroxyindoline, N-acetyl-5,6-dihydroxyindoline-2-carboxylic acid, 5-acetoxy-6-hydroxyindoline, and 5-acetoxy-6-hydroxyindoline-2-carboxylic acid.

Examples of the salt of the compound represented by the general formula (1) include a hydrochloride, a hydrobromide, a sulfate, a phosphate, an acetate, a propionate, a lactate, and a citrate of the foregoing compounds. Above all, a hydrobromide is preferred from the viewpoint of availability.

In the general formula (1), when $R^2$ is —COOH, examples of the salt of the compound represented by the general formula (1) include carboxylates thereof ($R^2$ is —COO⁻X⁺ (X⁺ is a cation, such as an alkali metal ion, e.g., Na⁺ and K⁺, an alkaline earth metal ion, e.g., Ca⁺ and Mg⁺, and an ammonium ion)).

From the viewpoint of dyeing the hair in a natural color shade, the component (A) is preferably one or more selected from the group consisting of 5,6-dihydroxyindole, 5,6-dihydroxyindole-2-carboxylic acid, 5,6-dihydroxyindoline, and 5,6-dihydroxyindoline-2-carboxylic acid, and salts thereof; more preferably one or more selected from the group consisting of 5,6-dihydroxyindole, 5,6-dihydroxyindole-2-carboxylic acid, and 5,6-dihydroxyindoline hydrobromide; still more preferably one or two selected from the group consisting of 5,6-dihydroxyindole and 5,6-dihydroxyindole-2-carboxylic acid; and yet still more preferably a combination of 5,6-dihydroxyindole and 5,6-dihydroxyindole-2-carboxylic acid.

In the case of use of a combination of 5,6-dihydroxyindole and 5,6-dihydroxyindole-2-carboxylic acid, a molar ratio thereof is preferably in a range of 50/50 to 99/1, more preferably in a range of 80/20 to 99/1, and still more preferably in a range of 85/15 to 95/5. When the molar ratio of 5,6-dihydroxyindole to 5,6-dihydroxyindole-2-carboxylic acid falls within the aforementioned range, finish of the hair after hair dyeing becomes close to a natural color tint.

The molar ratio of 5,6-dihydroxyindole to 5,6-dihydroxyindole-2-carboxylic acid can be quantitatively determined by means of reversed phase HPLC.

From the viewpoint of improvement in hair dyeing properties, the content of the component (A) in the hair cosmetic is preferably 0.05% by mass or more, more preferably 0.07% by mass or more, still more preferably 0.10% by mass or more, and yet still more preferably 0.20% by mass or more, and from the viewpoint of economy, it is preferably 5% by mass or less, more preferably 2% by mass or less, still more preferably 1.0% by mass or less, yet still more preferably 0.80% by mass or less, even yet still more preferably 0.50% by mass or less, and even still more preferably 0.40% by mass or less.

<Component (B)>

The hair cosmetic of the present invention contains a dimethylsilicone as the component (B). When the component (B) is contained, the touch during rinsing of hair after the treatment with the hair cosmetic of the present invention and the touch of hair after the treatment are improved. It should be construed that the component (B) in the present invention refers to an unmodified dimethylsilicone.

The component (B) is preferably a dimethylpolysiloxane, and more preferably a dimethylpolysiloxane represented by the following general formula (b).

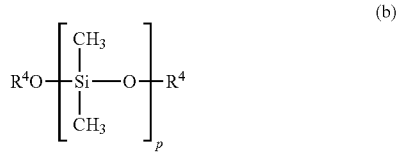

(b)

In the formula, $R^4$ represents $Si(CH_3)_3$ or a hydrogen atom; and p represents a number of 3 or more and 20,000 or less.

As the component (B) which is used in the present invention, the dimethylsilicone, and preferably the dimethylpolysiloxane represented by the general formula (b) can be used alone or in combination of two or more thereof. Above all, from the viewpoint of improvement in touch during rinsing of hair and improvement in touch of hair after the treatment, as the component (B), it is preferred to use a combination of (B) a dimethylpolysiloxane having a number average polymerization degree of less than 1,000 with (B2) a dimethylpolysiloxane having a number average polymerization degree of 1,000 or more (highly polymerized dimethylpolysiloxane); it is more preferred to use a combination of (B1) a dimethylpolysiloxane having a number average polymerization degree of 300 to 800 with (B2) a dimethylpolysiloxane having a number average polymerization degree of 1,000 to 5,000; and it is still more preferred to use a combination of (B1) a dimethylpolysiloxane having a number average polymerization degree of 450 to 650 with (B2) a dimethylpolysiloxane having a number average polymerization degree of 2,000 to 3,500. In the case where these are combined with each other, a mass ratio of the component (B1) to the component (B2) is preferably 10/90 to 99/1, more preferably 30/70 to 95/5, still more preferably 50/50 to 95/5, and yet still more preferably 60/40 to 80/20.

Among the dimethylpolysiloxanes, examples of a commercially available product of the component (B1) (number average polymerization degree: less than 1,000) include SH200 Series (e.g., SH200 C Fluid 1CS, SH200 C Fluid 2CS, SH200 C Fluid 5CS, SH200 C Fluid 10CS, SH200 C Fluid 20CS, SH200 C Fluid 30CS, SH200 C Fluid 50CS, SH200 C Fluid 100CS, SH200 C Fluid 200CS, SH200 C Fluid 350CS, SH200 C Fluid 500CS, SH200 C Fluid 1,000CS, SH200 C Fluid 5,000CS, SH200 Fluid 1.5CS, SH200 Fluid 3,000CS, SH200 Fluid 10,000CS, SH200 Fluid 12,500CS, and SH200 Fluid 30,000CS, all of which are manufactured by Dow Corning Toray Co., Ltd.), TSF-451 Series (manufactured by Momentive Performance Materials Inc.), and KF-96 Series (manufactured by Shin-Etsu Chemical Co., Ltd.). In addition, emulsions of these dimethylpolysiloxanes can also be used.

Among the dimethylpolysiloxanes, examples of a commercially available product of the component (B2) (number average polymerization degree: 1,000 or more) include SH200 Series (e.g., SH200 Fluid 60,000CS, SH200 Fluid 100,000CS, and SH200 Fluid 1,000,000CS, all of which are manufactured by Dow Corning Toray Co., Ltd.), TSF451-100MA (manufactured by Momentive Performance Materials Inc.), BY11-026 (manufactured by Dow Corning Toray Co., Ltd.; a diluted solution of highly polymerized dimethylpolysiloxane with a low-viscosity silicone), KF9008 (manufactured by Shin-Etsu Chemical Co., Ltd.; a diluted solution of highly polymerized dimethylpolysiloxane with a cyclic silicone), BY22-050A (manufactured by Dow Corning Toray Co., Ltd.; a cation emulsion of highly polymerized dimethylpolysiloxane), BY22-060 (manufactured by Dow Corning Toray Co., Ltd.; a cation emulsion of a solution of highly polymerized dimethylpolysiloxane diluted with a low-viscosity silicone), BY22-020 (manufactured by Dow Corning Toray Co., Ltd.; a cation emulsion of a solution of highly polymerized dimethylpolysiloxane diluted with liquid paraffin), and KM904 (manufactured by Shin-Etsu Chemical Co., Ltd.; a cation emulsion of a solution of highly polymerized dimethylpolysiloxane diluted with a low-viscosity silicone).

Among the aforementioned commercially available products, BY11-026, BY22-060, and BY11-039 (all of which are manufactured by Dow Corning Toray Co., Ltd.), and KF9008 and KM904 (all of which are manufactured by Shin-Etsu Chemical Co., Ltd.), each being a diluted material of highly polymerized dimethylpolysiloxane with a low-viscosity of silicone, and so on can be used as a commercially available product of a mixture of the component (B1) and the component (B2).

From the viewpoint of improvement in touch during rinsing of hair and improvement in touch of hair after the treatment, the content of the component (B) in the hair cosmetic of the present invention is preferably 0.01% by mass or more, more preferably 0.1% by mass or more, still more preferably 0.15% by mass or more, yet still more preferably 0.30% by mass or more, and even yet still more preferably 0.34% by mass or more, and from the viewpoint of improvement in touch of hair after the treatment and after the drying, it is preferably 5% by mass or less, more preferably 3% by mass or less, still more preferably 2% by mass or less, and yet still more preferably 1% by mass or less.

<Component (C)>

The hair cosmetic of the present invention contains an amino-modified silicone as the component (C). In view of the fact that the hair cosmetic of the present invention contains the component (B) and the component (C) in specified ratios, both the touch during rinsing of hair after the treatment with the hair cosmetic and the touch during rinsing of hair resulted when after the treatment, rinsing and drying are performed, and shampooing is further performed are improved.

The amino-modified silicone that is the component (C) may be a silicone having an amino group or an ammonium group. For example, the component (C) may be any of an amino-modified silicone in which all or a part of terminal hydroxy groups are blocked by a methyl group or the like and an amodimethicone in which terminal hydroxy groups are not blocked, and it may also be a poly(N-acylalkyleneimine)-modified silicone.

Preferred examples of the amino-modified silicone include those represented by the following general formula (c1) or (c2). In addition, emulsions of these amino-modified silicones can also be used.

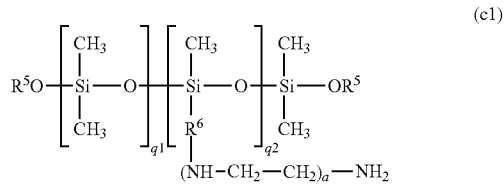

(c1)

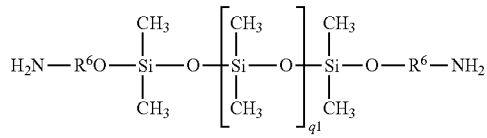

(c2)

In the formulae, $R^5$ represents $Si(CH_3)_3$ or a hydrogen atom; Re represents an alkylene group having 2 or more and 8 or less carbon atoms; q1 represents a number of 1 or more and 20,000 or less; q2 represents a number of 1 or more and 2,000 or less; and a is a number of 0 or more and 3 or less.

From the viewpoint of improvement in lubricity of the hair surface, improvement in touch during rinsing of hair after the treatment, and improvement in touch of hair after the treatment, the nitrogen content in the amino-modified silicone represented by the general formula (c1) or (c2) is preferably 0.02% by mass or more, and more preferably 0.05% by mass or more, and it is preferably 4% by mass or less, and more preferably 1% by mass or less.

As the component (C) which is used in the present invention, one or more of amino-modified silicones, and preferably amino-modified silicones represented by the general formula (c1) or (c2) can be used. From the viewpoint of improving both the squeaky feeling during rinsing of hair after the treatment and the squeaky feeling of the hair resulted when after the treatment, shampooing is further performed, as for the component (C), preferably, two or more amino-modified silicones are preferably contained; two or more amino-modified silicones selected from the group consisting of the amino-modified silicones represented by the general formulae (c1) and (c2) are more preferably used; and a combination of the amino-modified silicone represented by the general formula (c1) and the amino-modified silicone represented by the general formula (c2) is still more preferably used.

Examples of a combination of two or more amino-modified silicones include combinations of amino-modified silicones which are different from each other in terms of nitrogen content, polymerization degree, molecular structure, form (e.g., an emulsion, an oil, and a gum), or the like. Of these, a combination of two or more amino-modified silicones which are different from each other in terms of nitrogen content or form.

Examples of a combination of amino-modified silicones which are different from each other in terms of form include a combination of (C) an amino-modified silicone oil with (C2) an emulsion of an amino-modified silicone. For example, a highly polymerized amino-modified silicone oil having a number average polymerization degree of 1,000 or more readily fixes on the hair, whereas it is liable to generate squeaky feeling of the hair. Then, when using jointly the emulsion of an amino-modified silicone, slipperiness becomes favorable owing to an effect of the emulsion with a small particle diameter, the squeaky feeling during rinsing of hair after the treatment and the squeaky feeling of the hair resulted when after the treatment, shampooing is further performed are improved, and the touch of hair after the treatment can be more improved.

As for a mass ratio in the case of combing these, a mass ratio of the amino-modified silicone oil (C1) to the silicone component in the emulsion of the amino-modified silicone (C2) is preferably 1/99 to 90/10, more preferably 5/95 to 70/30, still more preferably 5/95 to 60/40, yet still preferably 10/90 to 60/40, and even yet still more preferably 10/90 to 40/60.

Examples of a commercially available product of the amino-modified silicone include amino-modified silicone oils, such as SF8451C (manufactured by Dow Corning Toray Co., Ltd., viscosity: 600 mm$^2$/s, nitrogen content: 0.8% by mass), SF8452C (manufactured by Dow Corning Toray Co., Ltd., viscosity: 700 mm$^2$/s, nitrogen content: 0.2% by mass), SF8457C (manufactured by Dow Corning Toray Co., Ltd., viscosity: 1,200 mm$^2$/s, nitrogen content: 0.8% by mass), KF8003 (manufactured by Shin-Etsu Chemical Co., Ltd., viscosity: 1,850 mm$^2$/s, nitrogen content: 0.7% by mass), KF8005 (manufactured by Shin-Etsu Chemical Co., Ltd., viscosity: 1,200 mm$^2$/s, nitrogen content: 0.1% by mass), KF867 (manufactured by Shin-Etsu Chemical Co., Ltd., viscosity: 1,300 mm$^2$/s, nitrogen content: 0.8% by mass), and KF8012 (manufactured by Shin-Etsu Chemical Co., Ltd., viscosity: 90 mm$^2$/s, nitrogen content: 0.6% by mass); and amodimethicone emulsions, such as SM8704C (manufactured by Dow Corning Toray Co., Ltd., nitrogen content: 0.8% by mass), SM8904C (manufactured by Dow Corning Toray Co., Ltd., nitrogen content: 0.3% by mass), BY22-079 (manufactured by Dow Corning Toray Co., Ltd., nitrogen content: 0.6% by mass), and XS65-C0032 (manufactured by Momentive Performance Materials Inc., nitrogen content: 0.1% by mass).

As a mixture of the component (B) and the component (C), CF1046 (manufactured by Dow Corning Toray Co., Ltd., nitrogen content: 0.14% by mass) that is a mixture of a dimethylpolysiloxane (number average polymerization degree: 550), a dimethylpolysiloxane (number average polymerization degree: 2,700), and an amino-modified silicone (mass ratio: 10/3.7/2.9) and the like can be suitably used.

From the viewpoint of improvement in touch during rinsing of hair after the treatment and improvement in touch of hair after the treatment, the content of the component (C) in the hair cosmetic of the present invention is preferably 0.003% by mass or more, more preferably 0.01% by mass or more, still more preferably 0.03% by mass or more, yet still more preferably 0.1% by mass or more, and even yet still more preferably 0.15% by mass or more, and from the viewpoint of touch after drying of hair and suppressing stickiness of hair, it is preferably 5% by mass or less, more preferably 3% by mass or less, and still more preferably 2% by mass or less.

From the viewpoint of improvement in touch during rinsing of hair after the treatment, the nitrogen content in the component (C) is preferably 0.10% by mass or more, more preferably 0.15% by mass or more, and still more preferably 0.20% by mass or more, and from the viewpoint of availability, it is preferably 0.80% by mass or less, more preferably 0.75% by mass or less, still more preferably 0.60% by mass or less, yet still more preferably 0.50% by mass or less, and even yet still more preferably 0.40% by mass or less.

From the viewpoint of improvement in touch during rinsing of hair after the treatment, the nitrogen content in the total amount of the component (B) and the component (C), both of which are a silicone component, is preferably 0.03% by mass or more, more preferably 0.04% by mass or more, still more preferably 0.05% by mass or more, and yet still more preferably 0.10% by mass or more, and it is preferably 0.40% by mass or less, more preferably 0.30% by mass or less, and still more preferably 0.20% by mass or less.

In the hair cosmetic of the present invention, a mass ratio of the component (C) to the component (B) [(C)/(B)] is 0.3 or more and 3.0 or less.

From the viewpoint of improvement in touch during rinsing of hair after the treatment and improvement in squeaky feeling during rinsing of hair resulted when after the treatment, rinsing and drying are performed, and shampooing is further performed, the mass ratio (C)/(B) is preferably 0.35 or more, more preferably 0.4 or more, still more preferably 0.45 or more, yet still more preferably 0.5 or more, and even yet still more preferably 0.6 or more, and from the same viewpoint, it is preferably 2.8 or less, more preferably 2.5 or less, still more preferably 1.5 or less, yet still more preferably 1.1 or less, and even yet still more preferably 1.0 or less. In addition, the mass ratio (C)/(B) is preferably 0.35 to 2.8, more preferably 0.4 to 2.8, still more preferably 0.4 to 2.5, yet still more preferably 0.45 to 2.5, even yet still more preferably 0.5 to 1.5, even still more preferably 0.5 to 1.1, even still more further preferably 0.5 to 1.0, and even yet still more further preferably 0.6 to 1.0.

The hair cosmetic of the present invention satisfies such a condition that a mass ratio of the component (A) to the component (B) and component (C) {(A)/[(B)+(C)]} is 1.0 or less. In view of the fact that the hair cosmetic of the present invention contains the component (A), the mass ratio (A)/[(B)+(C)] is a value of more than 0.

From the viewpoint of improvement in touch during rinsing of hair after the treatment and improvement in squeaky feeling during rinsing of hair resulted when after the treatment, rinsing and drying are performed, and shampooing is further performed, the mass ratio (A)/[(B)+(C)] is preferably 0.9 or less, more preferably 0.8 or less, still more preferably 0.7 or less, and yet still more preferably 0.6 or less, and it is preferably 0.01 or more, more preferably 0.04 or more, still more preferably 0.05 or more, yet still more preferably 0.1 or more, and even yet still more preferably 0.15 or more. In addition, from the same viewpoint, the mass ratio (A)/[(B)+(C)] is preferably 0.01 to 0.9, more preferably 0.01 to 0.8, still more preferably 0.04 to 0.7, yet still more preferably 0.05 to 0.7, and even yet still more preferably 0.1 to 0.6.

In the hair cosmetic of the present invention, from the viewpoint of improvement in touch during rinsing of hair after the treatment and improvement in squeaky feeling during rinsing of hair resulted when after the treatment, rinsing and drying are performed, and shampooing is further performed, it is preferred that not only the mass ratio (C)/(B) of the component (C) to the component (B) is 0.4 to 2.8, but also the mass ratio (A)/[(B)+(C)] is 0.01 to 0.8; it is more preferred that not only the mass ratio (C)/(B) is 0.4 to 2.5, but also the mass ratio (A)/[(B)+(C)] is 0.05 to 0.7; and it is still more preferred that not only the mass ratio (C)/(B) is 0.5 to 1.1, and but also the mass ratio (A)/[(B)+(C)] is 0.1 to 0.6.

<Surfactant>

The hair cosmetic of the present invention can further contain a surfactant. Examples of the surfactant include a cationic surfactant, a nonionic surfactant, an ampholytic surfactant, and an anionic surfactant. Of these, from the viewpoint of dispersibility and formulation stability of the silicone component, a nonionic surfactant is preferably contained, and from the viewpoint of improvement in touch of the hair, a cationic surfactant is preferably contained.

(Nonionic Surfactant)

From the viewpoint of dispersibility and formulation stability of the silicone, examples of the nonionic surfactant include a polyoxyalkylene alkyl ether, a polyoxyalkylene alkenyl ether, a polyoxyalkylene fatty acid ester, a higher fatty acid sucrose ester, a polyglycerin fatty acid ester, a polyoxyethylene hydrogenated castor oil, a polyoxyethylene sorbitan fatty acid ester, a polyoxyethylene sorbitol fatty acid ester, an alkyl saccharide, an alkylamine oxide, and an alkylamidoamine oxide. Of these, one or more selected from the group consisting of a polyoxyalkylene alkyl ether, a polyoxyethylene hydrogenated castor oil, and an alkyl saccharide are preferred, and a polyoxyethylene alkyl ether is more preferred.

In the case where the hair cosmetic contains a nonionic surfactant, from the viewpoint of dispersibility and formulation stability of the silicone, the content thereof in the hair cosmetic is preferably 0.01% by mass or more, and more preferably 0.02% by mass or more, and from the viewpoint of suppressing a lowering of touch of the hair, it is preferably 5% by mass or less, and more preferably 3% by mass or less.

(Cationic Surfactant)

Examples of the cationic surfactant include a mono- or di-long chain alkyl quaternary ammonium salt represented by the following general formula.

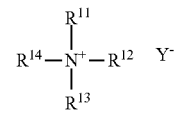

In the formula, $R^{11}$ represents a linear or branched alkyl group having 8 or more and 22 or less carbon atoms, or a group represented by $R^{15}CONH(CH_2)_m$—. $R^{15}$—O—$(CH_2)_m$—, or $R^{15}COO(CH_2)_m$— ($R^{15}$ represents a linear or branched alkyl group having 7 or more and 21 or less carbon atoms, and m represents a number of 1 or more and 4 or less); $R^{12}$ represents a linear or branched alkyl group having 1 or more and 22 or less carbon atoms, or a group represented by the foregoing $R^{15}CONH(CH_2)_m$—, $R^{15}$—O—$(CH_2)_m$—, or $R^{15}COO(CH_2)_m$—; $R^{13}$ and $R^{14}$ each independently represent an alkyl group having 1 or more and 4 or less carbon atoms; and Y represents a chloride ion, a bromide ion, or a methosulfate ion.

In the aforementioned general formula, preferably, $R^{11}$ represents a linear or branched alkyl group having 8 or more and 22 or less carbon atoms, or a group represented by $R^{15}$—O—$(CH_2)_m$— ($R^{15}$ represents a linear or branched alkyl group having 7 or more and 21 or less carbon atoms, and m represents a number of 1 or more and 4 or less); $R^{12}$ represents a linear or branched alkyl group having 1 or more and 22 or less carbon atoms, or a group represented by the aforementioned $R^{15}$—O—$(CH_2)_m$—; $R^{13}$ and $R^{14}$ each independently represent an alkyl group having 1 or more and 4 or less carbon atoms; and $Y^-$ represents a chloride ion.

The carbon number of the linear or branched alkyl group in $R^{11}$ is 8 or more and 22 or less, and preferably 8 or more and 18 or less.

The carbon number of the linear or branched alkyl group having 1 or more and 22 or less carbon atoms in $R^{12}$ is preferably 1 or more and 4 or less, and more preferably 1 or more and 3 or less in the case of a mono-long chain alkyl quaternary ammonium salt; and it is preferably 8 or more and 22 or less, and more preferably 8 or more and 18 or less in the case of a di-long chain alkyl quaternary ammonium salt.

$R^{13}$ and $R^{14}$ are each independently a hydrogen atom or an alkyl group having 1 or more and 4 or less carbon atoms, and preferably a methyl group.

The carbon number of the linear or branched alkyl group in $R^{15}$ is 7 or more and 21 or less, and preferably 7 or more and 19 or less.

As specific examples of the cationic surfactant, from the viewpoint of imparting an excellent touch to the hair, one or more selected from the group consisting of a monoalkyltrimethylammonium chloride, a dialkyldimethylammonium chloride, a monoalkyloxyalkyltrimethylammonium chloride, and a monoalkyltrimethylammonium bromide are preferred. Above all, one or more selected from the group consisting of behenyltrimethylammonium chloride, stearyltrimethylammonium chloride (steartrimonium chloride), cetyltrimethylammonium chloride (cetrimonium chloride), lauryltrimethylammonium chloride (lauryltrimonium chloride), a dialkyl(C12-C18)dimethylammonium chloride, and octadecyloxypropyltrimethylammonium chloride are more preferred.

In the case where the hair cosmetic contains a cationic surfactant, from the viewpoint of giving excellent touch to the hair, the content thereof in the hair cosmetic is preferably 0.01% by mass or more, and more preferably 0.05% by mass or more, and from the viewpoint of suppressing a lowering of touch of the hair, it is preferably 10% by mass or less, and more preferably 5% by mass or less.

(Anionic Surfactant)

In the case where the hair cosmetic is a hair cleansing agent, it preferably contains an anionic surfactant. Examples of the anionic surfactant include an alkylbenzene sulfonate, an alkyl or alkenyl ether sulfate, an alkyl or alkenyl sulfate, an olefin sulfonate, an alkane sulfonate, a saturated or unsaturated fatty acid salt, an alkyl or alkenyl ether carboxylate, an α-sulfo fatty acid salt, a N-acylamino acid, a phosphoric acid mono- or diester, and a sulfosuccinic acid ester. One or more of these anionic surfactants can be used.

Examples of a counter ion of an anionic group of the anionic surfactant include an alkali metal ion, such as a sodium ion and a potassium ion; an alkaline earth metal ion, such as a calcium ion and a magnesium ion; an ammonium ion; and an alkanolamine having 1 to 3 alkanol groups having 2 or 3 carbon atoms (for example, monoethanolamine, diethanolamine, triethanolamine, and triisopropanolamine).

In the case where the hair cosmetic contains an anionic surfactant, from the viewpoint of favorable lathering and easiness for washing in the case where the hair cosmetic is a hair cleansing agent, the content thereof is preferably 3% by mass or more, more preferably 5% by mass or more, and still more preferably 8% by mass or more. In addition, from the viewpoint of improvement in hair dyeing properties and suppression of any damage to the hair, it is preferably 40% by mass or less, more preferably 30% by mass or less, still more preferably 20% by mass or less, and yet still more preferably 15% by mass or less.

(Ampholytic Surfactant)

Examples of the ampholytic surfactant include a betaine-based surfactant, such as an alkyl dimethyl amino acetic acid betaine, a fatty acid amidopropylbetaine, and an alkylhydroxy sulfobetaine; and a sultaine-based surfactant, such as lauryl hydroxysultaine.

In the case where the hair cosmetic contains an ampholytic surfactant, from the viewpoint of adaptability to hair and favorable lathering, the content thereof in the hair cosmetic is preferably 0.05% by mass or more, more preferably 0.1% by mass or more, and still more preferably 0.15% by mass or more, and it is preferably 15% by mass or less, more preferably 12% by mass or less, and still more preferably 10% by mass or less.

<Other Components>

The hair cosmetic of the present invention may appropriately contain, in addition to the aforementioned components, a component which is typically used for hair cosmetics, within a range where the purpose of the present invention is not impaired. Examples of the foregoing component include an alkaline agent, a higher alcohol, an oil, an antioxidant, a pH adjustor, a dyeing agent other than the component (A), an aqueous medium, a polymer, an aromatic alcohol, an anti-dandruff agent, a vitamin compound, a disinfectant, an antiinflammatory agent, an antiseptic, a chelating agent, a humectant, a pearlescent agent, a ceramide, a perfume, and an ultraviolet absorber.

(Alkaline Agent)

It is preferred that the hair cosmetic of the present invention contains an alkaline agent. The alkaline agent has not only an action to swell the hair, thereby opening the cuticle and penetrating a dyeing agent component, such as the component (A), into the interior of the hair, but also an action to promote a polymerization reaction of the component (A), thereby improving the hair dyeing properties. As the alkaline agent, any material can be used without particular limitations so long as it is an alkaline agent that is used for usual hair dyes.

Examples of the alkaline agent include ammonia; alkanolamines, such as mono-, di-, or tri-methanolamine and mono-, di-, or tri-ethanolamine; alkylamines, such as methylamine, dimethylamine, ethylamine, diethylamine, N-methylethylamine, propylamine, and butylamine; aralkylamines, such as benzylamine; and inorganic alkaline compounds, such as sodium hydroxide and potassium hydroxide, and one or more of these materials can be used. The carbon number of the alkanolamine, alkylamine, or aralkylamine is preferably 10 or less, and more preferably 8 or less from the viewpoint of water solubility.

Above all, from the viewpoint of hair dyeing properties, the alkaline agent is preferably one or more selected from the group consisting of ammonia, an alkanolamine, an alkylamine, an aralkylamine, sodium hydroxide, and potassium hydroxide. The hair cosmetic of the present invention more preferably contains one or more of ammonia and an alkanolamine, still more preferably contains a monoalkanolamine, and yet still more preferably contains monoethanolamine.

From the viewpoint of improvement in hair dyeing properties, the content of the alkaline agent in the hair cosmetic is preferably 0.01% by mass or more, more preferably 0.1% by mass or more, and still more preferably 0.5% by mass or more, and from the viewpoint of suppressing irritation, it is preferably 10% by mass or less, more preferably 7.5% by mass or less, and still more preferably 5% by mass or less.

(Higher Alcohol)

The hair cosmetic of the present invention can contain a higher alcohol. In the case where the hair cosmetic is a hair cosmetic selected from the group consisting of a hair rinse, a hair conditioning agent, and a hair treatment agent, emulsification stability is improved, and in the case where the hair cosmetic is a hair cleansing agent, there is brought an effect, such as improvement in lathering.

As the higher alcohol, one represented by a general formula: $R^{31}$—OH [wherein $R^{31}$ represents a linear or branched hydrocarbon group having 12 or more and 24 or less carbon atoms] can be used. $R^{31}$ is preferably a linear or branched aliphatic hydrocarbon group having 12 or more and 24 or less carbon atoms; more preferably a linear or branched alkyl group having 12 or more and 24 or less carbon atoms or a linear or branched alkenyl group having 12 or more and 24 or less carbon atoms; and still more preferably a linear alkyl group having 12 or more and 24 or less carbon atoms or a linear alkenyl group having 12 or more and 24 or less carbon atoms.

Examples of the higher alcohol include lauryl alcohol, myristyl alcohol, cetyl alcohol, stearyl alcohol, isostearyl alcohol, arachidyl alcohol, behenyl alcohol, carnaubyl alcohol, and oleyl alcohol. The higher alcohol can be used alone or in combination of two or more thereof.

In the case where the hair cosmetic contains the higher alcohol, from the viewpoint of improvement in emulsification stability, the content thereof is preferably 0.1% by mass or more, more preferably 0.5% by mass or more, and still more preferably 1% by mass or more, and it is preferably 20% by mass or less, more preferably 15% by mass or less, and still more preferably 10% by mass or less.

(Oil)

From the viewpoint of improvement in touch of the hair, the hair cosmetic of the present invention can contain an oil. Examples of the oil include hydrocarbons, such as squalene, squalane, liquid paraffin, liquid isoparaffin, and cycloparaffin; glycerides, such as castor oil, cacao oil, mink oil, avocado oil, and olive oil; waxes, such as beeswax, spermaceti wax, lanolin, and carnauba wax; esters, such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids, such as capric acid, lauric acid, myristic acid, palmitic acid, stearic acid, behenic acid, oleic acid, coconut oil fatty acid, isostearic acid, and isopalmitic acid; and besides, isostearyl glyceryl ether and polyoxypropylene butyl ether. The oil can be used alone or in combination of two or more thereof.

In the case where the hair cosmetic contains the oil, from the viewpoint of improvement in touch of the hair, the content thereof is preferably 0.2% by mass or more, more preferably 0.3% by mass or more, and still more preferably 0.5% by mass or more, and from the viewpoint of suppressing a lowering of touch of the hair, it is preferably 10% by mass or less, more preferably 8% by mass or less, and still more preferably 5% by mass or less.

(Antioxidant)

Examples of the antioxidant include sulfurous acid, ascorbic acid, thioglycolic acid, L-cysteine, and N-acetyl-L-cysteine, and salts thereof. From the viewpoint of stabilization of the component (A) and improvement in hair dyeing properties, ascorbic acid and a salt thereof are preferred.

In the case of using the antioxidant, the content thereof in the hair cosmetic is preferably 0.01% by mass or more, and more preferably 0.05% by mass or more, and it is preferably 2% by mass or less, and more preferably 1% by mass or less.

(pH Adjustor)

From the viewpoint of adjusting the pH to an optimum range for polymerization of the component (A), thereby improving the hair dyeing properties, the hair cosmetic of the present invention can contain a pH adjustor. In the case where the hair cosmetic contains the aforementioned alkaline agent, a protonating agent is preferred as the pH adjustor. The protonating agent may be any of a monobasic acid and a polybasic acid, and may be any of an organic acid (the carbon number is 1 or more and 8 or less, provided that ascorbic acid is excluded) and an inorganic acid. As the protonating agent, one or more selected from the group consisting of hydrochloric acid, sulfuric acid, phosphoric acid, formic acid, acetic acid, and citric acid are exemplified, and one or two selected from the group consisting of phosphoric acid and citric acid are more preferred.

In the case of using the pH adjustor, though the content thereof is not particularly limited so long as it is an amount at which the pH of the hair cosmetic can be adjusted to a desired range, it is preferably 0.05% by mass or more, more preferably 0.1% by mass or more, and still more preferably 0.2% by mass or more. In addition, from the viewpoint of formulation stability, the content of the pH adjustor is preferably 5.0% by mass or less, more preferably 4.0% by mass or less, and still more preferably 3.5% by mass or less.

(Dyeing Agent Other than Component (A))

The hair cosmetic of the present invention may further contain a dyeing agent other than the component (A). Examples of the foregoing dyeing agent include an oxidation dye (constituted of a precursor and a coupler) and a direct dye, each of which is typically used for hair dyes.

As the dying agent other than the component (A), one or more materials can be used. The foregoing dyeing agent is preferably an oxidation dye. As the precursor, paraphenylenediamine, toluene-2,5-diamine, paraaminophenol, 4-aminometacresol, 1-hydroxyethyl-4,5-diaminopyrazole, and salts thereof are preferred; and as the coupler, 2,4-diaminophenoxyethanol, metaaminophenol, 2-methyl-5-aminophenol [=5-aminoorthocresol], resorcin, 2-methylresorcin, 4-chlororesorcinol, 1-naphthol, 2-amino-3-hydroxypyridine, 2-amino-4-(β-hydroxyethyl)aminoanisole, and salts thereof are preferred.

In the case of using the dyeing agent other than the component (A), the content thereof in the hair cosmetic is preferably 0.01% by mass or more, more preferably 0.02% by mass or more, and still more preferably 0.05% by mass or more, and it is preferably 1% by mass or less, and more preferably 0.5% by mass or less.

(Aqueous Medium)

The hair cosmetic typically contains an aqueous medium. Examples of the aqueous medium include water; a lower alcohol, such as ethanol and isopropyl alcohol; and a low-molecular diol or triol having 6 or less carbon atoms, such as 1,3-butylene glycol, glycerin, ethylene glycol, and propylene glycol, with water being preferred. Although the content of the aqueous medium in the hair cosmetic can be appropriately selected according to the formulation of the hair cosmetic, it is typically in a range of 1 to 95% by mass. In the case of using water as the aqueous medium, from the viewpoint that on the occasion when the hair cosmetic is diluted with water during use, coacervation is produced to adsorb the component (A) onto the hair surface, thereby revealing high hair dyeing properties, the content of water in the hair cosmetic is preferably 50% by mass or more, more preferably 60% by mass or more, and still more preferably 70% by mass, and it is preferably 95% by mass or less, and more preferably 90% by mass or less.

<pH>

From the viewpoint of improvement in hair dyeing properties, a pH of the hair cosmetic of the present invention is preferably 8.0 or more, more preferably 8.5 or more, and still more preferably 9.0 or more. This is because the component (A) that is the melanin precursor reacts with oxygen in air under a basic condition, whereby it is liable to be converted into a melanin pigment. From the viewpoint of improvement in hair dyeing properties and suppression of any damage to the hair, the foregoing pH is preferably 12.0 or less, more preferably 11.0 or less, and still more preferably 10.5 or less.

The aforementioned pH is a measured value at 25° C., and specifically, it can be measured by a method described in the section of Examples.

A production method of the hair cosmetic of the present invention is not particularly limited. For example, the hair cosmetic of the present invention can be produced by blending the components (A) to (C), and other components which are used, if desired by a method described in the section of Examples and mixing the blend by using a known stirring device or the like.

By applying the hair cosmetic of the present invention on hair, the hair can be dyed. Examples of the dyeing method of hair include a method of daily repeating steps of applying the hair cosmetic on hair and optionally cleansing. It is able to readily perform dyeing of gray hair and the like through a daily hair care behavior.

Regarding the aforementioned embodiments, the present invention discloses the following hair cosmetics.

<1> A hair cosmetic containing the following components (A) to (C):

(A) 0.05% by mass or more and 2% by mass or less of a compound represented by the following general formula (1) or a salt thereof:

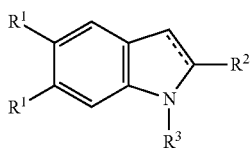

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) 0.1% by mass or more and 3% by mass or less of a dimethylsilicone; and (C) 0.1% by mass or more and 3% by mass or less of an amino-modified silicone, the hair cosmetic satisfying such conditions that a mass ratio of the component (C) to the component (B) [(C)/(B)] is 0.3 or more and 3.0 or less; and a mass ratio of the component (A) to the component (B) and component (C) {(A)/[(B)+(C)]} is 1.0 or less.

<2> A hair cosmetic containing the following components (A) to (C):

(A) 0.05% by mass or more and 2% by mass or less of a compound represented by the following general formula (1) or a salt thereof:

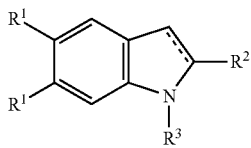

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a dimethylsilicone; and (C) an amino-modified silicone, the hair cosmetic satisfying such conditions that a mass ratio of the component (C) to the component (B) [(C)/(B)] is 0.35 or more and 2.8 or less; and a mass ratio of the component (A) to the component (B) and component (C) {(A)/[(B)+(C)]} is 0.01 or more and 0.8 or less.

<3> A hair cosmetic containing the following components (A) to (C):

(A) 0.10% by mass or more and 1.0% by mass or less of a compound represented by the following general formula (1) or a salt thereof:

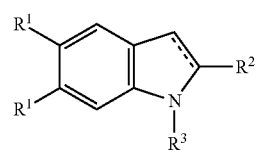

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a dimethylsilicone; and (C) an amino-modified silicone, the hair cosmetic satisfying such conditions that a mass ratio of the component (C) to the component (B) [(C)/(B)] is 0.45 or more and 2.5 or less; and a mass ratio of the component (A) to the component (B) and component (C) {(A)/[(B)+(C)]} is 0.04 or more and 0.7 or less.

<4> A hair cosmetic containing the following components (A) to (C):

(A) 0.05% by mass or more and 0.80% by mass or less of a compound represented by the following general formula (1) or a salt thereof:

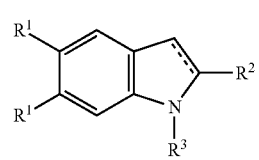

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) a dimethylsilicone; and (C) an amino-modified silicone, the hair cosmetic satisfying such conditions that a mass ratio of the component (C) to the component (B) [(C)/(B)] is 0.5 or more and 1.1 or less; and a mass ratio of the component (A) to the component (B) and component (C) {(A)/[(B)+(C)]} is 0.1 or more and 0.6 or less.

<5> A hair cosmetic containing the following components (A) to (C):

(A) 0.05% by mass or more and 1.0% by mass or less of one or more selected from the group consisting of 5,6- dihydroxyindole, 5,6-dihydroxyindole-2-carboxylic acid, and 5,6-dihydroxyindoline hydrobromide;

(B) (B1) a dimethylpolysiloxane having a number average polymerization degree of 300 to 800 and (B2) a dimethylpolysiloxane having a number average polymerization degree of 1,000 to 5,000; and (C) (C1) an amino-modified silicone oil and (C2) an emulsion of an amino-modified silicone, the hair cosmetic satisfying such conditions that a mass ratio of the component (C) to the component (B) [(C)/(B)] is 0.45 or more and 2.5 or less; and a mass ratio of the component (A) to the component (B) and component (C) {(A)/[(B)+(C)]} is 0.04 or more and 0.7 or less.

<6> A hair cosmetic containing the following components (A) to (C):

(A) 0.05% by mass or more and 1.0% by mass or less of a compound represented by the following general formula (1) or a salt thereof:

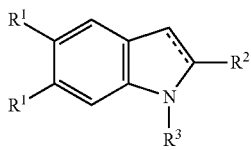

(1)

wherein a broken line represents the presence or absence of a π bond; $R^1$ represents a hydroxy group or an acetoxy group; $R^2$ represents a hydrogen atom or —COOR (R is a hydrogen atom, a methyl group, or an ethyl group); and $R^3$ represents a hydrogen atom, an acetyl group, a methyl group, or an ethyl group;

(B) 0.3% by mass or more and 3% by mass or less of a dimethylpolysiloxane; and (C) 0.15% by mass or more and 5% by mass or less of an amino-modified silicone, the hair cosmetic satisfying such conditions that the nitrogen content in the component (C) is 0.15% by mass or more and 0.6% by mass or less; a mass ratio of the component (C) to the component (B) [(C)/(B)] is 0.45 or more and 2.5 or less; and a mass ratio of the component (A) to the component (B) and component (C) {(A)/[(B)+(C)]} is 0.05 or more and 0.7 or less.

<7> A hair cosmetic containing the following components (A) to (C):

(A) 0.05% by mass or more and 1.0% by mass or less of one or more selected from the group consisting of 5,6-dihydroxyindole, 5,6-dihydroxyindole-2-carboxylic acid, and 5,6-dihydroxyindoline hydrobromide;

(B) 0.3% by mass or more and 3% by mass or less of a dimethyl silicone containing (B1) a dimethylpolysiloxane having a number average polymerization degree of 300 to 800 and (B2) a dimethylpolysiloxane having a number average polymerization degree of 1,000 to 5,000; and (C) 0.15% by mass or more and 5% by mass or less of an amino-modified silicone containing one or more amino-modified silicones represented by the following general formulae (c1) and (c2):

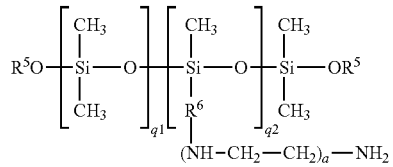

(c1)

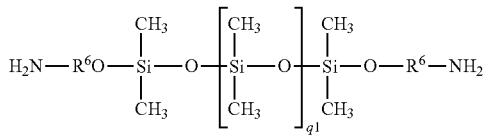

(c2)

wherein $R^5$ represents $Si(CH_3)_3$ or a hydrogen atom; $R^6$ represents an alkylene group having 2 or more and 8 or less carbon atoms; q1 represents a number of 1 or more and 20,000 or less; q2 represents a number of 1 or more and 2,000 or less; and a is a number of 0 or more and 3 or less, the hair cosmetic satisfying such conditions that the nitrogen content in the component (C) is 0.15% by mass or more and 0.6% by mass or less; a mass ratio of the component (C) to the component (B) [(C)/(B)] is 0.45 or more and 2.5 or less; and a mass ratio of the component (A) to the component (B) and component (C) {(A)/[(B)+(C)]} is 0.05 or more and 0.7 or less.

<8> A hair cosmetic containing the following components (A) to (C):

(A) 0.05% by mass or more and 1.0% by mass or less of one or more selected from the group consisting of 5,6-dihydroxyindole, 5,6-dihydroxyindole-2-carboxylic acid, and 5,6-dihydroxyindoline hydrobromide;

(B) 0.3% by mass or more and 3% by mass or less of a dimethyl silicone containing (B1) a dimethylpolysiloxane having a number average polymerization degree of 300 to 800 and (B2) a dimethylpolysiloxane having a number average polymerization degree of 1,000 to 5,000; and (C) 0.15% by mass or more and 5% by mass or less of an amino-modified silicone containing one or more amino-modified silicones represented by the following general formulae (c1) and (c2):

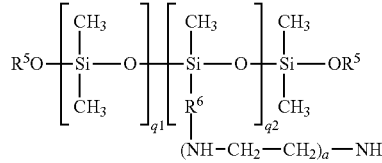

(c1)

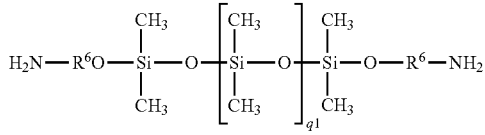

(c2)

wherein $R^5$ represents $Si(CH_3)_3$ or a hydrogen atom; $R^6$ represents an alkylene group having 2 or more and 8 or less carbon atoms; q1 represents a number of 1 or more and 20,000 or less; q2 represents a number of 1 or more and 2,000 or less; and a is a number of 0 or more and 3 or less, the hair cosmetic satisfying such conditions that the nitrogen content in the component (C) is 0.15% by mass or more and 0.6% by mass or less; a mass ratio of the component (C) to the component (B) [(C)/(B)] is 0.45 or more and 2.5 or less; a mass ratio of the component (A) to the component (B) and component (C) {(A)/[(B)+(C)]} is 0.05 or more and 0.7 or less; and a mass ratio (B1)/(B2) is 50/50 to 95/5.

<9> A hair cosmetic containing the following components (A) to (C):

(A) 0.10% by mass or more and 1.0% by mass or less of one or more selected from the group consisting of 5,6-dihydroxyindole, 5,6-dihydroxyindole-2-carboxylic acid, and 5,6-dihydroxyindoline hydrobromide;

(B) (B1) a dimethylpolysiloxane having a number average polymerization degree of 300 to 800 and (B2) a dimethylpolysiloxane having a number average polymerization degree of 1,000 to 5,000; and (C) (C1) an amino-modified silicone oil and (C2) an amino-modified silicone emulsion, the hair cosmetic satisfying such conditions that a mass ratio of the component (C) to the component (B) [(C)/(B)] is 0.45 or more and 2.5 or less; a mass ratio of the component (A) to the component (B) and component (C) {(A)/[(B)+(C)]} is 0.04 or more and 0.7 or less; and a mass ratio (C1)/(C2) is 5/95 to 60/40.

<10> A hair cosmetic containing the following components (A) to (C):

(A) 0.10% by mass or more and 1.0% by mass or less of one or more selected from the group consisting of 5,6-dihydroxyindole, 5,6-dihydroxyindole-2-carboxylic acid, and 5,6-dihydroxyindoline hydrobromide;

(B) (B1) a dimethylpolysiloxane having a number average polymerization degree of 300 to 800 and (B2) a dimethylpolysiloxane having a number average polymerization degree of 1,000 to 5,000; and (C) (C1) an amino-modified silicone oil and (C2) an amino-modified silicone emulsion, the hair cosmetic satisfying such conditions that a mass ratio of the component (C) to the component (B) [(C)/(B)] is 0.45 or more and 2.5 or less; a mass ratio of the component (A) to the component (B) and component (C) {(A)/[(B)+(C)]} is 0.04 or more and 0.7 or less; and a mass ratio (B1)/(B2) is 50/50 to 95/5.

<11> The hair cosmetic as set forth in any one of <1> to <5>, <9>, and <10>, wherein the nitrogen content in the component (C) is 0.10% by mass or more and 0.80% by mass or less.

<12> The hair cosmetic asset forth in anyone of <1> to <4> and <6>, wherein the component (C) contains two or more amino-modified silicones.

<13> The hair cosmetic as set forth in any one of <1> to <12>, further containing a nonionic surfactant.

<14> The hair cosmetic as set forth in any one of <1> to <13>, further containing a cationic surfactant.

<15> The hair cosmetic as set forth in any one of <1> to <14>, wherein a pH at 25° C. is 8.0 or more and 12.0 or less.

<16> The hair cosmetic as set forth in any one of <1> to <15>, wherein a pH at 25° C. is 8.5 or more and 11.5 or less.

<17> The hair cosmetic asset forth in any one of <1> to <16>, wherein a pH at 25° C. is 9.0 or more and 11.0 or less.

EXAMPLES

The present invention is hereunder described by reference to Examples, but it should be construed that the present invention is not limited to the scope of the Examples.

[pH Measurement]

A pH at 25° C. of the hair cosmetic was measured with a pH meter (F-51, manufactured by HORIBA, Ltd.).

Preparation of Hair Cosmetic (Hair Conditioning Agent)

Examples 1 to 22 and Comparative Examples 1 to 6

Among the blending components shown in Table 1, the components (B) and (C), the nonionic surfactant, and a part of water were mixed to prepare a uniform silicone emulsion. Subsequently, other components than ascorbic acid and the component (A) were mixed to prepare an aqueous solution, which was then mixed with the silicone emulsion, to obtain a mixed liquid. To the obtained mixed liquid, ascorbic acid and a solution of the component (A) were added in a nitrogen atmosphere and uniformly mixed, to prepare a hair cosmetic. All of the hair cosmetics had a pH of 10.

[Evaluation of Hair Cosmetic (Touch Evaluation)]

For the touch evaluation, a black hair tress having a length of 30 cm and a mass of 10 g (BS-B3A, manufactured by Beaulax Co., Ltd.) was used.

The aforementioned black hair tress was cleansed once with a plain shampoo having a composition shown below and then air-dried. The resultant was further subjected to a bleach treatment once for 30 minutes, cleansed once with the plain shampoo, and then air-dried. This tress was subjected to the following evaluation.

| (Plain Shampoo) | (% by mass) |
|---|---|
| Sodium polyoxyethylene lauryl ether sulfate: | 57.4 |
| (EMAL E-27C (active component amount: 27% by mass), manufactured by Kao Corporation) | |
| Lauramide DEA: | 1.5 |
| (AMINON L-02, manufactured by Kao Corporation) | |
| EDTA-2Na: | 0.3 |
| (FROST DS, manufactured by Daiichi Pure Chemical Co., Ltd.) | |
| Phosphoric acid (adjusted at a pH of 7.0) | Moderate |
| Purified water | Remainder |
| Total | 100 |

The tress for evaluation which had been rinsed with warm water for 30 seconds in advance was shampooed with the aforementioned plain shampoo for 15 seconds and then rinsed with warm water for 30 seconds. 5 g of the hair cosmetic obtained in each of the Examples was uniformly applied on this tress in a bath ratio of 1/0.5/0.5 (tress/water/hair cosmetic) and then allowed to stand in an atmosphere at 30° C. for 5 minutes, thereby treating the tress.

Subsequently, the tress after the treatment was rinsed with warm water for 30 seconds, to wash away the hair cosmetic, followed by drying with a towel and then drying with a dryer. Furthermore, the tress was again rinsed with warm water for 30 seconds, shampooed with the aforementioned plain shampoo for 15 seconds, and then rinsed with warm water for 30 seconds.

In the aforementioned steps, the touch evaluation was performed at two points of time including a time when the tress after the treatment was rinsed with the hair cosmetic (evaluation 1) and a time when the tress after the evaluation 1 was dried, further shampooed, and then rinsed (evaluation 2). Six expert panelists evaluated at the time of combing fingers through the tress from the root of the hair toward the hair end direction. The evaluation value was determined in terms of a number of panelists who evaluated "smooth and favorable touch without being caught".

TABLE 1

| | | | Example | | | | | | | | | | | |
|---|---|---|---|---|---|---|---|---|---|---|---|---|---|---|
| | | | 1 | 2 | 3 | 4 | 5 | 6 | 7 | 8 | 9 | 10 | 11 |
| Blend (% by mass) | (A) | (A1) 5,6-Dihydroxy-indole solution *1 | 30.00 | 30.00 | 5.00 | 30.00 | 5.00 | 30.00 | 30.00 | 30.00 | 30.00 | 30.00 | 30.00 |
| | | (A2) 5,6-Dihydroxy-indole solution *2 | | | | | | | | | | | |
| | | (A3) 5,6-Dihydroxy-indoline·HBr solution *3 | | | | | | | | | | | |
| | (B) | Dimethyl-polysiloxane *4 | 0.82 | 0.25 | 0.82 | 0.16 | 0.16 | 0.41 | 0.82 | 1.71 | 0.38 | 2.74 | 0.33 |
| | (C) | (C1) Aminoethyl-aminopropyl/ methylpolysiloxane copolymer (nitrogen content: 0.8% by mass) *5 | 0.18 | 0.05 | 0.18 | 0.04 | 0.04 | 0.09 | 0.18 | 0.38 | 0.06 | 0.60 | 0.05 |
| | | (C2) Highly polymerized aminoethyl-aminopropylmethyl-siloxane-dimethyl-siloxane copolymer emulsion (nitrogen content: 0.1% by mass) (40% emulsion) *6 | 1.00 | 0.30 | 1.00 | 1.00 | 1.00 | 1.00 | 1.00 | 3.34 | 0.33 | 8.76 | 0.28 |
| | Nonionic surfactant | Polyoxyethylene (25) cetyl ether *7 | | | | | | | | | | | |
| | | Polyoxyethylene (9) tridecyl ether *8 | | | | | | | | | | | |
| | Cationic surfactant | Stearyl trimethyl-ammonium chloride (28%) *9 | | | | | | | | | 3.00 | | |
| | Others | Monoethanolamine *10 | 3.00 | 3.00 | 3.00 | 3.00 | 3.00 | 3.00 | 3.00 | 3.00 | 3.00 | 3.00 | 3.00 |
| | | Ascorbic acid *11 | 0.30 | 0.30 | 0.30 | 0.30 | 0.30 | 0.30 | 0.30 | 0.30 | 0.30 | 0.30 | 0.30 |
| | | Phosphoric acid (75%) *12 | 1.50 | 1.50 | 1.50 | 1.50 | 1.50 | 1.50 | 1.50 | 1.50 | 1.50 | 1.50 | 1.50 |
| | | Oxidation dye X *13 | | | | | | | | | | | |
| | | Oxidation dye Y *14 | | | | | | | | | | | |
| | | Ion-exchanged water | 63.20 | 64.60 | 88.20 | 64.00 | 89.00 | 63.70 | 60.20 | 59.78 | 64.44 | 53.10 | 64.54 |
| | Total | | 100.00 | 100.00 | 100.00 | 100.00 | 100.00 | 100.00 | 100.00 | 100.00 | 100.00 | 100.00 | 100.00 |
| Content of component (A) (% by mass) | | | 0.34 | 0.34 | 0.06 | 0.34 | 0.06 | 0.34 | 0.34 | 0.34 | 0.34 | 0.34 | 0.34 |
| Content of component (B) (% by mass) | | | 0.82 | 0.25 | 0.82 | 0.16 | 0.16 | 0.41 | 0.82 | 1.71 | 0.38 | 2.74 | 0.33 |
| Content of components (B) and (C) (% by mass) | | | 1.40 | 0.42 | 1.40 | 0.60 | 0.60 | 0.90 | 1.40 | 3.42 | 0.57 | 6.84 | 0.49 |
| Total content of component (C) (% by mass) | | | 0.58 | 0.17 | 0.58 | 0.44 | 0.44 | 0.49 | 0.58 | 1.71 | 0.19 | 4.10 | 0.16 |
| Nitrogen content in component (C) (% by mass) | | | 0.31 | 0.31 | 0.31 | 0.16 | 0.16 | 0.22 | 0.31 | 0.25 | 0.32 | 0.20 | 0.31 |
| Nitrogen content in components (B) and (C) (% by mass) | | | 0.13 | 0.13 | 0.13 | 0.11 | 0.11 | 0.12 | 0.13 | 0.13 | 0.11 | 0.12 | 0.10 |
| (C)/(B) | | | 0.71 | 0.68 | 0.71 | 2.75 | 2.75 | 1.20 | 0.71 | 1.00 | 0.50 | 1.50 | 0.50 |
| (A)/[(B) + (C)] | | | 0.24 | 0.81 | 0.04 | 0.57 | 0.10 | 0.38 | 0.24 | 0.10 | 0.60 | 0.05 | 0.70 |
| Content of nonionic surfactant (% by mass) | Polyoxyethylene (7) cetyl ether | | 0.081 | 0.024 | 0.081 | 0.081 | 0.081 | 0.081 | 0.081 | 0.270 | 0.026 | 0.709 | 0.023 |
| | Polyoxyethylene (25) cetyl ether | | 0.016 | 0.005 | 0.016 | 0.016 | 0.016 | 0.016 | 0.016 | 0.053 | 0.005 | 0.140 | 0.005 |
| | Polyoxyethylene (9) tridecyl ether | | | | | | | | | | | | |
| Evaluation | (Evaluation 1) Touch during rinsing after the treatment | | 6 | 4 | 5 | 5 | 6 | 5 | 6 | 6 | 6 | 5 | 6 |
| | (Evaluation 2) Touch during rinsing resulted when after the evaluation1. the tress was dried and further shampooed | | 6 | 5 | 6 | 4 | 4 | 5 | 6 | 6 | 6 | 6 | 5 |

| | | | Example | | | | | | | | | | |
|---|---|---|---|---|---|---|---|---|---|---|---|---|
| | | | 12 | 13 | 14 | 15 | 16 | 17 | 18 | 19 | 20 | 21 | 22 |
| Blend (% by mass) | (A) | (A1) 5,6-Dihydroxy-indole solution *1 | 5.00 | 30.00 | 30.00 | 30.00 | 30.00 | 30.00 | 30.00 | | | 30.00 | 30.00 |
| | | (A2) 5,6-Dihydroxy-indole solution *2 | | | | | | | | | 30.00 | | |

TABLE 1-continued

| | | | | | | | | | | | | | |
|---|---|---|---|---|---|---|---|---|---|---|---|---|---|
| | | (A3) 5,6-Dihydroxy-indoline•HBr solution *3 | | | | | | | | | 30.00 | | |
| | (B) | Dimethyl-polysiloxane *4 | 1.63 | 0.31 | 0.26 | 1.14 | 0.36 | 0.82 | 0.82 | 0.82 | 0.82 | 0.82 | 0.82 |
| | (C) | (C1) Aminoethyl-aminopropyl/methylpolysiloxane copolymer (nitrogen content: 0.8% by mass) *5 | 0.70 | 0.05 | 0.03 | 0.25 | 0.08 | 0.58 | | 0.18 | 0.18 | 0.18 | 0.18 |
| | | (C2) Highly polymerized aminoethyl-aminopropylmethyl-siloxane-dimethyl-siloxane copolymer emulsion (nitrogen content: 0.1% by mass) (40% emulsion) *6 | 8.43 | 0.18 | 0.12 | 2.22 | 0.34 | | 1.45 | 1.00 | 1.00 | 1.00 | 1.00 |
| Nonionic surfactant | | Polyoxyethylene (25) cetyl ether *7 | | | | | | 0.10 | | | | | |
| | | Polyoxyethylene (9) tridecyl ether *8 | | | | | | | | | | | |
| Cationic surfactant | | Stearyl trimethyl-ammonium chloride (28%) *9 | | | | | | | | | | | |
| Others | | Monoethanolamine *10 | 3.00 | 3.00 | 3.00 | 3.00 | 3.00 | 3.00 | 3.00 | 3.00 | 3.00 | 3.00 | 3.00 |
| | | Ascorbic acid *11 | 0.30 | 0.30 | 0.30 | 0.30 | 0.30 | 0.30 | 0.30 | 0.30 | 0.30 | 0.30 | 0.30 |
| | | Phosphoric acid (75%) *12 | 1.50 | 1.50 | 1.50 | 1.50 | 1.50 | 1.50 | 1.50 | 0.08 | 0.08 | 0.08 | 0.08 |
| | | Oxidation dye X *13 | | | | | | | | | | 0.035 | |
| | | Oxidation dye Y *14 | | | | | | | | | | | 0.035 |
| | | Ion-exchanged water | 79.44 | 64.66 | 64.78 | 61.59 | 64.43 | 63.70 | 62.93 | 64.62 | 64.62 | 64.59 | 64.59 |
| | | Total | 100.00 | 100.00 | 100.00 | 100.00 | 100.00 | 100.00 | 100.00 | 100.00 | 100.00 | 100.00 | 100.00 |
| Content of component (A) (% by mass) | | | 0.06 | 0.34 | 0.34 | 0.34 | 0.34 | 0.34 | 0.34 | 0.30 | 0.30 | 0.34 | 0.34 |
| Content of component (B) (% by mass) | | | 1.63 | 0.31 | 0.26 | 1.14 | 0.36 | 0.82 | 0.82 | 0.82 | 0.82 | 0.82 | 0.82 |
| Content of components (B) and (C) (% by mass) | | | 5.70 | 0.43 | 0.34 | 2.28 | 0.57 | 1.40 | 1.40 | 1.40 | 1.40 | 1.40 | 1.40 |
| Total content of component (C) (% by mass) | | | 4.07 | 0.12 | 0.08 | 1.14 | 0.21 | 0.58 | 0.58 | 0.58 | 0.58 | 0.58 | 0.58 |
| Nitrogen content in component (C) (% by mass) | | | 0.22 | 0.39 | 0.37 | 0.25 | 0.36 | 0.80 | 0.10 | 0.32 | 0.32 | 0.32 | 0.32 |
| Nitrogen content in components (B) and (C) (% by mass) | | | 0.16 | 0.11 | 0.08 | 0.13 | 0.13 | 0.33 | 0.04 | 0.13 | 0.13 | 0.13 | 0.13 |
| (C)/(B) | | | 2.50 | 0.40 | 0.30 | 1.00 | 0.60 | 0.71 | 0.71 | 0.71 | 0.71 | 0.71 | 0.71 |
| (A)/[(B) + (C)] | | | 0.01 | 0.80 | 1.00 | 0.15 | 0.60 | 0.24 | 0.24 | 0.21 | 0.21 | 0.24 | 0.24 |
| Content of nonionic surfactant (% by mass) | | Polyoxyethylene (7) cetyl ether | 0.683 | 0.015 | 0.010 | 0.180 | 0.027 | | 0.118 | 0.081 | 0.081 | 0.081 | 0.081 |
| | | Polyoxyethylene (25) cetyl ether | 0.135 | 0.003 | 0.002 | 0.036 | 0.005 | 0.100 | 0.023 | 0.016 | 0.016 | 0.016 | 0.016 |
| | | Polyoxyethylene (9) tridecyl ether | | | | | | | | | | | |
| Evaluation | (Evaluation 1) | Touch during rinsing after the treatment | 5 | 5 | 4 | 6 | 6 | 4 | 5 | 6 | 6 | 6 | 6 |
| | (Evaluation 2) | Touch during rinsing resulted when after the evaluation1. the tress was dried and further shampooed | 6 | 4 | 3 | 6 | 6 | 3 | 4 | 6 | 6 | 6 | 6 |

| | | | Comparative Example | | | | | |
|---|---|---|---|---|---|---|---|---|
| | | | 1 | 2 | 3 | 4 | 5 | 6 |
| Blend (% by mass) | (A) | (A1) 5,6-Dihydroxy-indole solution *1 | 30.00 | 30.00 | 30.00 | 30.00 | 30.00 | 30.00 |
| | | (A2) 5,6-Dihydroxy-indole solution *2 | | | | | | |
| | | (A3) 5,6-Dihydroxy-indoline•HBr solution *3 | | | | | | |
| | (B) | Dimethyl-polysiloxane *4 | 0.54 | 0.19 | | 1.65 | 0.04 | 2.48 |
| | (C) | (C1) Aminoethyl-aminopropyl/methylpolysiloxane copolymer (nitrogen content: 0.8% by mass) | 0.30 | 0.04 | | 0.35 | 0.01 | 0.53 |

TABLE 1-continued

|  |  | | | | | | |
|---|---|---|---|---|---|---|---|
|  | (C2) Highly polymerized aminoethyl-aminopropylmethyl-siloxane-dimethyl-siloxane copolymer emulsion (nitrogen content: 0.1% by mass) (40% emulsion) *6 | 3.59 | 0.18 | 2.03 |  | 0.10 |  |
| Nonionic surfactant | Polyoxyethylene (25) cetyl ether *7 |  |  |  | 0.10 |  |  |
|  | Polyoxyethylene (9) tridecyl ether *8 |  |  |  |  |  | 1.50 |
| Cationic surfactant | Stearyl trimethylammonium chloride (28%) *9 |  |  |  |  |  |  |
| Others | Monoethanolamine *10 | 3.00 | 3.00 | 3.00 | 3.00 | 3.00 | 0.50 |
|  | Ascorbic acid *11 | 0.30 | 0.30 | 0.30 | 0.30 | 0.30 | 0.30 |
|  | Phosphoric acid (75%) *12 | 1.50 | 1.50 | 1.50 | 1.50 | 1.50 | 1.50 |
|  | Oxidation dye X *13 |  |  |  |  |  |  |
|  | Oxidation dye Y *14 |  |  |  |  |  |  |
|  | Ion-exchanged water | 60.76 | 64.78 | 63.18 | 63.10 | 65.05 | 63.19 |
| Total |  | 100.00 | 100.00 | 100.00 | 100.00 | 100.00 | 100.00 |
| Content of component (A) (% by mass) | | 0.34 | 0.34 | 0.34 | 0.34 | 0.34 | 0.34 |
| Content of component (B) (% by mass) | | 0.54 | 0.19 | 0.00 | 1.65 | 0.04 | 2.48 |
| Content of components (B) and (C) (% by mass) | | 2.28 | 0.31 | 0.81 | 2.00 | 0.09 | 3.01 |
| Total content of component (C) (% by mass) | | 1.74 | 0.12 | 0.81 | 0.35 | 0.05 | 0.53 |
| Nitrogen content in component (C) (% by mass) | | 0.22 | 0.36 | 0.10 | 0.80 | 0.22 | 0.80 |
| Nitrogen content in components (B) and (C) (% by mass) | | 0.17 | 0.13 | 0.10 | 0.14 | 0.12 | 0.14 |
| (C)/(B) | | 3.20 | 0.60 | — | 0.21 | 1.25 | 0.21 |
| (A)/[(B) + (C)] | | 0.15 | 1.10 | 0.42 | 0.17 | 3.80 | 0.11 |
| Content of nonionic surfactant (% by mass) | Polyoxyethylene (7) cetyl ether | 0.291 | 0.015 | 0.162 |  | 0.008 |  |
|  | Polyoxyethylene (25) cetyl ether | 0.057 | 0.003 | 0.032 | 0.100 | 0.002 |  |
|  | Polyoxyethylene (9) tridecyl ether |  |  |  |  |  | 1.500 |
| Evaluation | (Evaluation 1) Touch during rinsing after the treatment | 4 | 2 | 4 | 2 | 2 | 1 |
|  | (Evaluation 2) Touch during rinsing resulted when after the evaluation1, the tress was dried and further shampooed | 2 | 2 | 1 | 3 | 1 | 4 |

The components described in Table 1 are shown below. All of the blending amounts (% by mass) described in the table are tangible.

*1: (A1) Solution produced by the method described in Japanese Patent No. 5570161 (5,6-dihydroxyindole: 1% by mass, 5,6-dihydroxyindole-2-carboxylic acid: 0.14% by mass, ethanol: 20% by mass, water: remainder)

*2: (A2) 5,6-Dihydroxyindole solution (manufactured by Matrix Scientific, 5,6-dihydroxyindole: 1% by mass, ethanol: 20% by mass, water: remainder)

*3: (A3) 5,6-Dihydroxyindoline hydrobromide solution (manufactured by AK-scientific, 5,6-dihydroxyindoline hydrobromide: 1% by mass, ethanol: 20% by mass, water: remainder)

*4: Silicone BY11-039 (manufactured by Dow Corning Toray Co., Ltd., (B1) 73% by mass of a dimethylpolysiloxane component having a number average molecular weight of 550 and (B2) 27% by mass of a dimethylpolysiloxane component having a number average molecular weight of 2,700)

*5: (C1) SF8457C (manufactured by Dow Corning Tray Co., Ltd., an amino-modified silicone oil)

*6: (C2) XS65-C0032 (manufactured by Momentive Performance Materials Inc., an amodimethicone emulsion, active component amount: 40% by mass, amount of nonionic surfactant: 9.7% by mass)

*7: NIKKOL BC-25 (manufactured by Nikko Chemicals Co., Ltd.)

*8: SOFTANOL 90 (manufactured by Nippon Shokubai Co., Ltd.)

*9: QUARTAMIN 86W (manufactured by Kao Corporation, active component amount: 28% by mass)

*10: Monoethanolamine (manufactured by Petronas Chemicals)

*11: Ascorbic acid (Japanese Pharmacopoeia Ascorbic Acid, manufactured by Watanabe Chemical Co., Ltd.)

*12: Food additive 75% phosphoric acid (manufactured by Nippon Chemical Industrial Co., Ltd.)

*13: Oxidation dye X: Toluene-2,5-diamine sulfate, paraaminophenol, metaaminophenol, resorcin, 2,4-diaminophenoxyethanol hydrochloride, 5-aminoorthocresol, and paraphenylenediamine sulfate, each of which is blended in an amount of 0.005% by mass (the amount relative to the whole amount of the hair cosmetic)

*14: Oxidation dye Y: 2-Methylresorcin, 4-aminometacresol, 2-amino-3-hydroxypyridine, 2-amino-4-(β-hydroxyethyl)aminoanisole sulfate, 4-chlororesorcinol, 1-naphthol, and 1-hydroxyethyl-4,5-diaminopyrazole sulfate, each of which is blended in an amount of 0.005% by mass (the amount relative to the whole amount of the hair cosmetic)

The following were noted from Table 1.

As in Examples 1 to 22, when the content ratios of the components (A), (B), and (C) in the hair cosmetic fall within the scope of the present invention, a favorable touch was obtained in all of the evaluation 1 and the evaluation 2. On the other hand, as in Comparative Examples 1 to 6, when the content ratios of the components (A), (B), and (C) in the hair cosmetic fall outside the scope of the present invention, it was noted that a favorable touch is not obtained in any one of the evaluation 1 and the evaluation 2.

INDUSTRIAL APPLICABILITY

In accordance with the hair cosmetic of the present invention, squeaky feeling during rinsing of hair after the treatment and squeaky feeling of the hair resulting from, after the treatment, performing rinsing and drying, and then further shampooing can be improved, and a touch of the hair after the treatment can be improved. In addition, it is able to readily perform dyeing of gray hair and the like through a daily hair care behavior.

The invention claimed is:

1. A hair cosmetic, comprising:
    (A) a compound represented by the following formula (1) or a salt thereof:

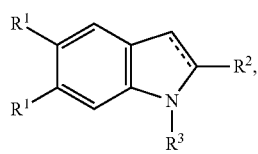

(1)

wherein a broken line represents the presence or absence of a π bond; $R^1$ represents a hydroxy group or an acetoxy group; $R^2$ represents a hydrogen atom or —COOR, where R is a hydrogen atom, a methyl group, or an ethyl group; and $R^3$ represents a hydrogen atom, an acetyl group, a methyl group, or an ethyl group;
    (B) a dimethylsilicone; and
    (C) an amino-modified silicone, wherein the (C) amino-modified silicone comprises a combination of (C1) an amino-modified silicone oil and (C2) an emulsion of an amino-modified silicone,
    wherein a mass ratio of the component (C) to the component (B) [(C)/(B)] is from 0.5 to 1.1; and a mass ratio of the component (A) to the component (B) and component (C) {(A)/[(B)+(C)]} is from 0.1 to 0.6, and
    wherein a nitrogen content in the component (C) is from 0.20% by mass to 0.40% by mass.

2. The hair cosmetic according to claim 1, wherein a content of the component (A) is from 0.05% by mass to 5% by mass.

3. The hair cosmetic according to claim 1, wherein a content of the component (B) is from 0.01% by mass to 5% by mass.

4. The hair cosmetic according to claim 1, wherein a content of the component (C) is from 0.01% by mass to 5% by mass.

5. The hair cosmetic according to claim 1, further comprising a nonionic surfactant.

6. The hair cosmetic according to claim 1, further comprising a cationic surfactant.

7. The hair cosmetic according to claim 1, wherein a pH at 25° C. is from 8.0 to 12.0.

8. The hair cosmetic according to claim 1, wherein the mass ratio of the component (C) to the component (B) [(C)/(B)] is from 0.6 to 1.1.

9. The hair cosmetic according to claim 1, wherein a mass ratio (C1)/(C2) is from 10/90 to 40/60.

10. The hair cosmetic according to claim 1, wherein the (B) dimethylsilicone comprises a combination of (B1) a dimethylpolysiloxane having a number average polymerization degree of less than 1,000 and (B2) a dimethylpolysiloxane having a number average polymerization degree of at least 1,000.

11. The hair cosmetic according to claim 10, wherein the (B) dimethylsilicone comprises a combination of (B1) a dimethylpolysiloxane having a number average polymerization degree of 300 to 800 and (B2) a dimethylpolysiloxane having a number average polymerization degree of 1,000 to 5,000.

* * * * *